(12) United States Patent
Jerusik et al.

(10) Patent No.: US 8,420,012 B2
(45) Date of Patent: Apr. 16, 2013

(54) USE OF MONOCHLOROUREA TO TREAT INDUSTRIAL WATERS

(75) Inventors: Russell J. Jerusik, Newark, DE (US); Maren David, Apple Valley, MN (US); Jay C. Henderson, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 372 days.

(21) Appl. No.: 12/823,253

(22) Filed: Jun. 25, 2010

(65) Prior Publication Data

US 2010/0331416 A1 Dec. 30, 2010

Related U.S. Application Data

(60) Provisional application No. 61/269,668, filed on Jun. 26, 2009.

(51) Int. Cl.
*A61L 2/18* (2006.01)
(52) U.S. Cl.
USPC ............................. 422/28; 210/749; 210/764
(58) Field of Classification Search .................... 422/28; 210/749, 764, 754
See application file for complete search history.

(56) References Cited

U.S. PATENT DOCUMENTS

| | | | |
|---|---|---|---|
| 2,106,513 A | 1/1938 | Allison | |
| 3,031,292 A | 4/1962 | Todd | 71/2.6 |
| 3,749,672 A | 7/1973 | Golton et al. | 252/95 |
| 3,948,967 A | 4/1976 | Krenzer et al. | 260/463 |
| 3,956,366 A | 5/1976 | Sheppard et al. | 260/482 |
| 3,972,706 A | 8/1976 | Arnold | 71/90 |
| 4,039,315 A | 8/1977 | Klauke et al. | 71/98 |
| 4,294,986 A | 10/1981 | Spatz et al. | 564/52 |
| 4,334,912 A | 6/1982 | Yoshida et al. | 71/94 |
| 4,364,769 A | 12/1982 | Pissiotas et al. | 71/90 |
| 4,418,038 A * | 11/1983 | Theeuwes | 422/37 |
| 4,422,871 A | 12/1983 | Schirmer et al. | 71/120 |
| 4,437,880 A | 3/1984 | Takahashi et al. | 71/120 |
| 4,678,503 A | 7/1987 | Barlet et al. | 71/93 |
| 5,158,596 A | 10/1992 | Sherba et al. | 71/67 |
| 5,241,117 A | 8/1993 | Maekawa et al. | 564/37 |
| 5,565,109 A | 10/1996 | Sweeny | 210/755 |
| 6,046,133 A | 4/2000 | Hewett et al. | 504/133 |
| 6,132,628 A | 10/2000 | Barak | 210/756 |
| 6,270,722 B1 | 8/2001 | Yang et al. | 422/37 |
| 6,669,904 B1 | 12/2003 | Yang et al. | 422/37 |
| RE39,021 E | 3/2006 | Sweeny | 210/755 |
| 7,311,878 B2 | 12/2007 | Singleton et al. | 422/37 |
| 2007/0045199 A1 | 3/2007 | Mayer et al. | 210/764 |
| 2007/0178173 A1 | 8/2007 | Rice et al. | 424/661 |

FOREIGN PATENT DOCUMENTS

| | | |
|---|---|---|
| EP | 0 069 705 | 7/1982 |
| EP | 0 078 555 | 9/1982 |
| WO | 9639296 | 12/1996 |
| WO | 2004032979 | 4/2004 |

OTHER PUBLICATIONS

International Search Report PCT/US2010/039922, dated Sep. 23, 2010, pp. 1-3.

* cited by examiner

*Primary Examiner* — Sean E Conley
(74) *Attorney, Agent, or Firm* — Joanne Rossi; Shaorong Chen; Michael J. Herman

(57) ABSTRACT

The present invention comprises a method for controlling (e.g. inhibiting) or killing microorganisms in an aqueous environment. The method includes the addition of an effective amount of monochlorourea or modified monochlorourea to an aqueous solution. This aqueous solution may be a cooling water system, a recreational water system, a water treatment facility, or any circulating water system (i.e. a papermaking facility). A method of producing monochlorourea or modified monochlorourea is also disclosed.

16 Claims, No Drawings

USE OF MONOCHLOROUREA TO TREAT INDUSTRIAL WATERS

CROSS-REFERENCE TO RELATED APPLICATIONS

This application claims priority to U.S. Provisional Application No. 61/269,668, filed Jun. 26, 2009, which is hereby incorporated by reference herein for all purposes.

FIELD OF THE INVENTION

The present invention relates to a method of controlling growth of microorganisms in aqueous systems, more particularly in industrial process waters.

BACKGROUND OF THE INVENTION

Uncontrolled growth of microorganisms in industrial production systems can have serious consequences such as lowered product quality, degradation or spoilage of products, contamination of products, and interference with a wide range of important industrial processes. Growth of microorganisms on surfaces exposed to water (e.g., recirculation systems, heat exchangers, once-through heating and cooling systems, pulp and paper process systems, etc.) can be especially problematic, as many of these systems provide an environment suitable for growth of bacteria and other types of microorganisms. Industrial process waters often provide conditions of temperature, nutrients, pH, etc. that allow for growth of microorganisms in the water and on submerged surfaces. Uncontrolled growth of microorganisms is often manifested in the water column with large numbers of free-floating (planktonic) cells as well as on submerged surfaces where conditions favor formation of biofilms.

Biofilm formation is a serious problem in aqueous industrial systems. Biofilm formation begins when planktonic cells contact submerged surfaces either as a result of turbulence in water flow or by active movement toward the surface. If conditions are favorable for growth, microorganisms can attach to the surface, grow, and begin to produce biopolymers that provide three-dimensional integrity to the biofilm. Over time, the biofilm becomes thicker and internally complex as cells reproduce and produce more biopolymers. The microbial community of a biofilm can consist of single or multiple species.

Many types of processes, systems, and products can be adversely affected by uncontrolled growth of microorganisms in biofilms and in industrial process waters. Such problems include accelerated corrosion of metals, accelerated decomposition of wood and other biodegradable materials, restricted flow through pipes, plugging or fouling of valves and flow-meters, and reduced heat exchange or cooling efficiency on heat exchange surfaces. Biofilms may also be problematic relative to cleanliness and sanitation in medical equipment, breweries, wineries, dairies and other industrial food and beverage process water systems. Moreover, sulfate-reducing bacteria are often problematic in waters used for the secondary recovery of petroleum or for oil drilling in general. Although sulfate-reducing bacteria can form biofilms on equipment and in pipelines, the significant problem caused by these bacteria is that they generate metabolic by-products that have highly offensive odors, are toxic, and can cause corrosion of metal surfaces by accelerating galvanic action. For example, these microorganisms reduce sulfates present in the injection water to generate hydrogen sulfide, a highly toxic gas that has a highly offensive odor (i.e., rotten egg odor), is corrosive, and reacts with metal surfaces to form insoluble iron sulfide corrosion products.

Paper production is particularly susceptible to adverse effects of biofilms. Paper process waters have conditions (e.g., temperature and nutrients) that favor growth of microorganisms in the water and on exposed surfaces. Biofilms in paper process systems are often referred to as slime or slime deposits and contain paper fiber and other materials used in paper production. Slime deposits can become dislodged from system surfaces and become incorporated into the paper, which results in holes and defects or breaks and tears in the sheet. Such problems result in a lower quality product or unacceptable product being rejected. This necessitates stopping paper production to clean the equipment, which results in the loss of production time.

In order to control problems caused by microorganisms in industrial process waters, numerous antimicrobial agents (i.e., biocides) have been employed to eliminate, to inhibit or to reduce microbial growth. Biocides are used alone or in combination to prevent or control the problems caused by growth of microorganisms. Biocides are usually added directly to a process water stream; the typical method of addition is such that the biocide is distributed throughout the process system. In this manner, planktonic microorganisms and those in biofilms on surfaces in contact with the process water can be controlled.

Depending on their chemical composition and mode-of-action, biocides are classified as oxidizing or non-oxidizing. Oxidizing and non-oxidizing biocides can be used alone or in combination, depending on the application. Oxidizing biocides have been widely used in industry for decades, especially in pulp and paper production where strong oxidizers have been used to control microbial populations. Oxidizing biocides such as chlorine gas, sodium hypochlorite, hypobromous acid, and chlorine dioxide are widely used as biocides to treat recirculating waters in many types of industries. Two of the primary reasons for using these and other oxidizing biocides is that such oxidizers are: (1) inexpensive; and (2) non-specific regarding which types of microorganisms are inhibited; if sufficient concentrations of oxidizing biocides are achieved virtually all microorganisms can be inhibited.

Of the oxidizing biocides, chlorine is the most widely used to treat recirculating water systems. The chemistry of chlorine is well known. When added to water, chlorine can exist in either of two forms, HOCl and OCl$^-$, depending on pH. These chemical species of chlorine, also referred to as "free chlorine," react with a wide variety of organic compounds in aqueous systems.

The highly reactive nature of chlorine may also be a liability, as some of the oxidizer will be used (e.g., consumed) during reactions with non-biological material. Therefore, in order to provide enough oxidizer to react with microorganisms in a process stream, the total amount of oxidizer needed to inhibit microorganisms will include that used in reactions with non-biological components of the system. Reactions with non-biological components of process water not only add to treatment cost, but undesired by-products can be generated and other additives in the process stream can be adversely affected.

Process streams such as in paper mills are especially problematic for highly reactive oxidizers because of the high concentrations of dissolved and particulate inorganic and organic materials. Such process waters exhibit a very high "demand" on the oxidizer. "Demand" is defined as the amount of chlorine that reacts with substances other than the target microorganisms in the process water. In order to maintain an effective concentration of chlorine in an aqueous system to inhibit microorganisms, an amount in excess of the demand must be applied. The types and amounts of inorganic and organic materials in a process stream will define the demand for an oxidizer. For example, many substances are known to react with chlorine and result in the chlorine being non-biocidal; such substances include sulfides, cyanides, metal ions, lignin, and, among others, various water treatment chemicals (e.g., some scale and corrosion inhibitors).

Although effective as biocides, strong oxidizers such as sodium hypochlorite can cause many problems in an industrial process stream such as increased corrosion rates, increased consumption of wet end additives, and, among others, decreased life of felts used on paper machines.

Because of the inherent reactivity of chlorine and related strong oxidizers with non-biological organic and inorganic materials, it is desirable to have the oxidizer in a form that would have antimicrobial activity but be less reactive with non-biological materials. It is known that chlorination of various nitrogen-containing organic and inorganic compounds can reduce the negative effects of chlorine on additives and equipment used in industrial settings. This lower reactivity may also allow the chlorinated nitrogen-species to penetrate a biofilm and react with the microorganisms, rather than be consumed in non-specific reactions with abiotic and inorganic materials in the water.

There remains a need for improved biocides that are effective under harsh environmental conditions such as found in the papermaking industry and other industrial processes.

N-chlorourea, also called monochlorourea (MCU), has been used in many applications, including bleaching (U.S. Pat. No. 3,749,672), delignification from cotton, and textile desizing, and has been used as an herbicide. MCU has also been used as a reaction intermediate in the synthesis of trans-2-chlorocyclopentanol and 2-chlorocyclohexanone. It has been shown that MCU is the initial reaction product in the formation of hydrazine, in which sodium hypochlorite is mixed with urea in the presence of gelatin.

SUMMARY OF THE INVENTION

The present invention comprises a method for the use of monochlorourea or modified monochloroureas in controlling microbial growth control in aqueous environments, more particularly in industrial process waters. The invention also provides for a method of producing monochlorourea or modified monochlorourea.

One aspect of the invention is a process comprising the step of adding an aqueous solution of monochlorourea or modified monochlorourea to an industrial water system to control the growth of microorganisms where the solution of monochlorourea or modified monochlorourea is such that greater than 20% of the solids on a molar basis are monochlorourea or modified monochlorourea.

Another aspect of the invention is a method of producing monochlorourea or modified monochlorourea, the method comprising the step of adding bleach at a rate of between 0.5 molar equivalents per hour and 20 equivalents per hour to an aqueous solution of urea wherein the pH of the urea is between 2 and 7 and the pH of the bleach is between 6 and 13 wherein the conversion of urea or modified urea to the monochlorourea or modified monochlorourea is greater than 20% on a molar basis.

Also disclosed is a method of producing monochlorourea or modified monochlorourea, the method comprising the steps of the adding a chlorine source, such as an alkyl hypochlorite, to a non aqueous solution or suspension of urea or modified urea followed by the isolation of the chlorourea as a solid or oil.

DETAILED DESCRIPTION OF THE INVENTION

The present invention relates to a method which can be applied to industrial process waters, such as pulp and paper process systems, to control the growth of both planktonic and biofilm-associated microorganisms. The present invention provides for monochlorourea or modified monochlorourea to be added to an industrial water system to control microbiological growth.

The method comprises adding monochlorourea or modified monochlorourea in an effective amount to an industrial process water system to control microbial growth. Industrial process water systems include but are not limited to cooling water system, a recreational water system, a water treatment facility, or any circulating water system (i.e. a papermaking facility).

While monochlorourea offers many advantages as a biocidal active, there are a number of other derivatives that can also be effective. Specifically, those with aliphatic, both linear and branched, or aromatic substituents at one or both of the N and/or N' positions. The advantages of these materials arise in their differing solubilities, stabilities, and abilities to partition into biofilms or across biological membranes. For example, by removing some of the protons from urea the formation of the deprotonated form that is believed to lead to decomposition is hindered. Additionally, substituents along the carbon backbone have the ability to provide further fine tuning to the reactivity and stability through electronic factors as well as their abilities to form stabilized ring intermediates. Furthermore, the addition of functional groups can also aid in determining the solubility, stability, and reactivity of the molecule as well as influence partitioning into biofilms and across the bacterial membrane.

Useful urea sources as a raw material to make a substituted monochlorourea can include substituted urea, for example N-monoalkyl urea, N,N'-dialkylurea, N,N-dialkylurea, and functionalized alkylurea.

Monochlorourea or substituted monchlorourea have the general formula:

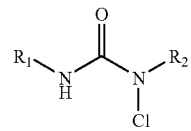

where $R_1$ and $R_2$, independently are H, or alkyl, aryl, or aromatic or other functionalized carbon chains having between 1 and 10 carbon atoms, The alkyl or aryl group can be linear or branched. The alkyl or aryl groups can have functional groups such as $CH_3$, COOH, Cl, Br, $NO_2$, $NH_2$, $SO_3H$ or OH.

In one preferred embodiment $R_1$ and $R_2$, independently are H or methyl or functionalized methyl groups.

Examples of monochlorourea or substituted monchlorourea include, but are not limited to, N-chlorourea, N,N'-dichlorourea, N-chloro-N,N'-dimethylurea, N-chloro-N-methylurea, N-chloro-N'-methylurea, and N-chloro-N,N'-bishydroxymethylurea.

In the present invention, monochlorourea and modified monochlorourea have been found to possess a high degree of antimicrobial activity in comparison to strong oxidizers, such as sodium hypochlorite. Monochlorourea and modified monochlorourea are less reactive, and as a result, more stable than sodium hypochlorite or other free chlorine-generating biocides. Urea is not a sequestrant, stabilizer, or adjuvant for hypochlorite.

The purity of the monochlorourea or modified monochlorourea that will be fed to the industrial water is at least 20% active on a dry solids molar basis monochlorourea or modified monochlorourea, preferably greater than 30% active monochlorourea or modified monochlorourea, preferably greater than 50% active monochlorourea or modified monochlorourea.

Effective concentrations of monochlorourea or modified monochlorourea in the industrial water system, on an active level basis, are from about 0.01 milligram per liter (mg/l) to about 1000 mg/l by weight, (i.e., based on the weight as measured by the amount of available chlorine [in mg/l]) and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. Thus, with respect to the biocides, the lower and upper limits of the required concentrations substantially depend upon the system to be treated.

Both monochlorourea and modified monochlorourea can be produced as liquids or solid, and can be fed into the water system as a liquid or a solid. If a solid product is desired for ease of delivery, but a liquid product is desired for ease of treatment, the solid product can be blended with water on-site and then fed to the industrial water system. Both materials can also be made on site by the addition of an oxidizing chlorine source.

The dosage amounts of the monochlorourea and modified monochlorourea required for effectiveness generally depend on the nature of the aqueous system being treated, the level of organisms present in the aqueous system, and the level of inhibition desired. A person skilled in the art, using the information disclosed herein could determine the amount necessary without undue experimentation.

Monochlorourea and modified monochlorourea are effective for controlling and inhibiting the growth and reproduction of microorganisms in aqueous systems and additive aqueous systems. Aqueous systems include industrial waters systems such as cooling water systems, pulp and paper systems, petroleum operations, industrial lubricants and coolants, lagoons, lakes, and ponds.

In addition, the aqueous systems in which the present invention can be used includes, but is not limited to, those involved in the processing, manufacture and/or use of paints, leather, wood, wood pulp, wood chips, starch, clays, retention aids, sizing agents, defoamers, dry and wet strength additives, pigment slurries (e.g., precipitated calcium carbonate), proteinaceous materials, lumber, animal hides, vegetable tanning liquors, cosmetics, toiletry and personal care formulations, emulsions, adhesives, coatings, metalworking fluids, swimming pool and spa water, textiles, heat exchangers, pharmaceutical and diagnostic reagent formulations, geological drilling lubricants, and agrochemical compositions.

Aqueous systems include additive aqueous systems. "Additive" is defined as a product or substance dissolved or suspended in water that is or will be added into a larger aqueous system. Examples of additives used in the pulp and paper industry include, but are not limited to, retention aids, sizing agents, defoamers, dry and wet strength additives and pigment slurries.

The choice of addition rate and pH can have a significant effect on the yield and product distribution for monochlorourea, as can be seen in Example 1. Through judicious choice of conditions N,N'-dichlorourea can also be obtained. The same is true for other urea derivatives as exemplified by the results for N,N'-dimethyl-N-chlorourea. The dimethylurea is less sensitive to the reaction conditions and near quantitative yields of chloro-dimethylurea can be isolated via slow addition or instantaneous addition rates as seen in Example 2. A slight excess of bleach is required if the pH of the dimethylurea solution is not acidic.

The production of monochlorourea or modified monochlorourea with the percent conversion of greater than 20% on a molar basis, preferably greater than 25%, and preferably greater than 30% to monochlorourea or modified monochlorourea in solution is achieved by addition of a chlorine source, such as bleach, to an aqueous solution of urea. The urea solution should be at a pH between 2-7, preferably between 2 and less than 5, and most preferably 2-4. The chlorine source or bleach solution should be at a pH between 5-13 and most preferably 5-8. It is preferable that there is at least a 1 pH unit difference between the pH of the urea solution and the pH of the chlorine source. Chlorine sources include, but are not limited to, commercial bleach, chlorine gas, N-chlorosuccinimide, salt of a hypochlorite or bleach generated on site electrolytically. The concentration of urea is preferably less that 25% by weight. The concentration of bleach is preferably less that 25% by weight. The concentration of the urea should be between 0.5-15% by weight, preferably between 0.5 and 10%, more preferably between 0.5 and 5% and the concentration of chlorine source or bleach should be between 1-15% by weight, preferably between 1 and 10%, more preferably between 1 and 5%. The pH of the final chlorourea or modified chlorourea is preferably less than 7. The pH of the final chlorourea or modified chlorourea product should be between 2 and 7, most preferably between 2 and 5. The effects of the changes made in these conditions can be seen in Examples 1 and 2.

In some aspects of the invention, the chlorine source or bleach addition rate is to be between 0.5 molar equivalents per hour and 20 equivalents per hour, preferably between 0.5 and 10 equivalents per hour, and most preferably between 0.5 and 4 equivalents per hour.

In one aspect of the invention a method for the production of monochlorourea is disclosed, the method comprising the step of adding a chlorine source, such as bleach, at a rate of between 0.5 molar equivalents per hour and 20 equivalents per hour, preferably 0.5 to 10 molar equivalents per hour, to a solution of urea wherein the pH of the urea is between 2 and 5, preferably between 2 and 4, and the pH of the chlorine source is between 5 and 13 wherein the conversion of urea to the monochlorourea is greater than 20% on a dry molar basis. It is preferred that the ratio of urea to chlorine source be between 1.5:1 to 1:5. It is more preferred that the molar ratio of urea to chlorine source be about equimolar ("about" being within 25%) up to an excess of bleach, such as 1:5.

Typically, urea or modified urea is reacted with a chlorine source in a molar ratio of urea to chlorine (as $Cl_2$) in the range of 5:1 to 1:5, preferably from 3:1 to 1:5, preferably from 2:1 to 1:5, preferably from 2:1 to 1:3 and more preferably from 1.5:1 to 1:3 and more preferably from 1.25:1 to 1:2. It is more preferred that the molar ratio of urea to chlorine source be about equimolar ("about" being within 25%) up to an excess of bleach, such as 1:5 or 1:3 or 1:2.

Monochlorourea can also be produced by adding tert-butyl hypochlorite to a solution of urea in a non aqueous solvent such as methanol. The solvent is removed by concentrating the reaction mixture under reduced pressure, and the resulting crystals of monochlorourea are collected. Modified monochloroureas such as dimethyl chlorourea and bis-hydroxymethyl chlorourea can be produced by the same method, but are often isolated as oils.

Urea should not be considered a nitrogen moiety (nitrogen source) in the same manner as ammonium. Urea is also known by the chemical names carbamide, carbonyl diamide, and carbonyl diamine among others. The proper chemical naming of the chemical group $CONH_2$ is a carbamide. The chemistry of the urea and oxidizer reaction is distinct from the reaction chemistry of amines with oxidizers as described in the Yang et. al. patents (U.S. Pat. No. 6,669,904 and U.S. Pat. No. 6,270,722) and Sweeney et. al. (U.S. Pat. No. 5,565,109).

As an example, it is well known that amines will protonate or deprotonate as a function of pH. The $NH_2$ groups in urea are significantly less prone to this protonation/deprotonation effect. The reactivity of the $NH_2$ groups in urea are distinct from typical amines because of the partial positive charge carried by the electron deficient carbonyl carbon alpha to the amine. This raises the pka of the amine above 26 (versus 5 for ammonia, 9 for $NH_4Cl$, 7 for alkyl amines, or 18 for sulfonamides). This pka difference is indicative of the significantly different chemical environment and nature of the nitrogens in urea and urea derivatives.

Chloramine compounds are typically produced at an alkaline pH of 8 or greater to enhance stability and biocidal performance; however, monochlorourea stability and biocidal efficacy do not require an alkaline pH. In fact, chlorourea and modified chloroureas are stable under a wide variety of pH conditions. They exhibit limited but significant stability under basic conditions, and are highly stable under acidic conditions. This can be seen in Examples 13 and 14.

Monochlorourea or modified monochlorourea can be generated in solutions with a wide pH range, preferably pH 2-8. It can be produced with very inexpensive raw materials while providing a significant improvement for industrial water treatment compared to currently used oxidizer based antibacterial systems.

In one embodiment of the invention the pH of the chlorourea prior to the addition to the water to be treated can be less than pH 8, less than pH 7 and less than pH 5. The pH of the aqueous chlorourea product can range from 2-8, preferably from 2-5, most preferable 2-4.

The chlorine sources useful in the invention can include, but are not limited to, chlorine, alkali earth metal—hypochlorite, alkaline earth metal—hypochlorite, organic hypochlorite, chlorine dioxide, chlorinated isocyanurates, electrolytically-generated hypochlorites, chlorinated hydantoins, and bromine chloride. The preferred source is alkaline earth metal hypochlorite.

Monobromourea and modified monobromoureas are also expected to act as biocides similar to monochlorourea and modified monochlorourea.

EXAMPLES

The following examples are intended to be illustrative of the present invention. However, these examples are not intended to limit the scope of the invention or its protection in any way.

Example 1

It was found that significant differences in the percent actives obtained in the final solution of chlorourea could be obtained depending on the conditions used (Table 1). Two types of addition rates were employed. In the instant addition two syringes, one containing a urea solution (15%) and the other containing bleach (13%), were rapidly injected through a t-mixer in order to generate the chlorourea solution. The product distribution, percent actives, and stability were somewhat affected by the initial pH of each solution, but the amount of the active relative to other products was never higher than 18%.

In the second type of addition the bleach was added at a much slower rate, between 0.5 and 2 molar equivalents per hour to a urea solution. In this slow method the urea was placed in 40-50 mL of water and the required amount of bleach was diluted up to 20 mL total volume with water. The bleach solution was subsequently added at rates from 0.33 mL/min up to 1 mL/min. The results are exemplified in Table 1. In the slow addition method, conversion rates of up to 71% were obtained for monochlorourea, with up to 15% dichlorourea. This represents a significant increase in the concentration of the active species.

TABLE 1

Yields of chlorourea and dichlorourea based on addition rates, pH, and concentrations.

| Exp # | Urea pH | Bleach pH | Addition Type | Urea:Bleach | % MCU | % DCU |
|---|---|---|---|---|---|---|
| 1A | native | 12.0 | instant | 3:1 | 16 | ~1 |
| 1B | native | 12.0 | instant | 1:3 | 0 | ~1 |
| 1C | native | 12.0 | instant | 1:1 | 18 | ~1 |
| 1D | native | 8.2 | instant | 1:1 | 15-20 | ~1 |
| 1E | 13.0 | 7.5 | instant | 1:1 | 7-8 | ~1 |
| 1F | 5.0 | 7.5 | instant | 1:1 | 17 | ~1 |
| 1G | 2.5 | 6.3 | slow | 1:1 | 68-69 | 9-10 |
| 1H | 2.5 | 5.8 | slow | 1:2 | 67 | 4 |
| 1J | 2.5 | 5.8 | slow | 1:3 | 71 | 14 |
| 1K | 2.5 | 5.8 | slow | 1:4 | 71 | 15 |
| 1L | 5.0 | 6.0 | slow | 1:1 | 14 | ~1 |

Example 2

The same experiment as in example 1 was conducted, using N,N'-dimethylurea (DMU) with different addition rates and initial pH, and indicated a similar trend (Table 2). The instant addition gave yields between 58-68%, but the slower addition rates, specifically those in which the DMU was in an acidic condition gave quantitative yields with only one molar equivalent of bleach.

TABLE 2

Yields of dimethylchlorourea based on addition rates, pH, and concentrations.

| Exp # | DMU pH | Bleach pH | Addition Type | DMU:Bleach | % DMCU |
|---|---|---|---|---|---|
| 2A | 2.5 | 12.0 | instant | 1:1 | 58 |
| 2B | 7.0 | 12.0 | instant | 1:1 | 68 |
| 2C | 2.5 | 12.0 | slow | 1:0.5 | 36 |
|  | 2.5 | 12.0 | slow | 1:1 | 100 |
| 2D | 7.0 | 12.0 | slow | 1:0.5 | 25 |
|  | 7.0 | 12.0 | slow | 1:1 | 58 |
|  | 7.0 | 12.0 | slow | 1:1.5 | 98 |

Example 3

Differences exist between monochlorourea and sodium hypochlorite, namely, sodium hypochlorite is a free chlorine generating biocide while monochlorourea is not. Free and total chlorine are measured using the DPD reagents from the Hach Company. The test is a colorimetric test in which more intense color development results as more oxidizing chlorine is present in the sample. The rate at which the dye reacts with the oxidizing chemical depends on whether the chlorine is free or bound. Total chlorine includes both free and bound chlorine.

The rate at which the dye reacts with total chlorine is accelerated by the addition of iodide to the test. This differentiates the free and total chlorine. The iodide reacts rapidly with bound oxidizing chlorine to form iodine and chloride. The iodine, a free oxidizing halogen, reacts very rapidly with the DPD dye.

One thousand ppm (as total $Cl_2$) solutions of monochlorourea and sodium hypochlorite were prepared in synthetic hard water with 250 ppm hardness. Total and free chlorine readings were taken at 0 minutes, 30 minutes, 2 hours, and 4 hours. Untreated hard water solutions were used as blanks. The samples were stored at 35° C.+/−2° C. with mild stirring. pH values are provided as a reference points for the conditions of the chlorine species at the various test times.

Table 3 compares duplicate samples of sodium hypochlorite and monochlorourea. Significant differences exist between the free and total chlorine values of these chemicals. The release of free chlorine from monochlorourea is an energetically unfavorable reaction. Monochlorourea is a combined chlorine species that functions to kill bacteria not as a donor of free chlorine, but as a biocide itself.

Procedure:
Made-up 1 Liter sample of synthetic hard water with 250 ppm hardness.
Took 100 mL aliquots and set up duplicate samples of biocides at least 1,000 ppm based on total Chlorine readings.
Monitored pH, free chlorine and total chlorines at timed intervals of—0 min, 30 min, 2 hours, and 4 hours,
Monitored un-treated (blank) hard water at time 0 to serve as baseline.
Between sampling stored all samples in 35° C.+/−2° C. Heater/shaker with mild stirring.

TABLE 3

Free Vs. Total Chlorine Values

| | Time = 0 | | | Time = 30 min | | | Time = 2 hours | | | Time = 4 hours | | |
|---|---|---|---|---|---|---|---|---|---|---|---|---|
| | Free Cl | Tot Cl | pH | Free Cl | Tot Cl | pH | Free Cl | Tot Cl | pH | Free Cl | Tot Cl | pH |
| Blank[1] | 10 | 0 | 7.9 | | | | | | | | | |
| MCU-1[2] | 0 | 1620 | 7.1 | 10 | 1500 | 7.1 | 10 | 1490 | 6.9 | 10 | 1230 | 6.6 |
| MCU-2 | 0 | 1190 | 7.2 | 20 | 1210 | 7.2 | 30 | 1120 | 6.9 | 20 | 1000 | 6.6 |
| Bleach-1[3] | 900 | 950 | 8.5 | 860 | 890 | 8.4 | 810 | 920 | 8.4 | 840 | 940 | 8.4 |
| Bleach-2 | 950 | 1060 | 8.5 | 880 | 1020 | 8.5 | 840 | 1010 | 8.3 | 950 | 1040 | 8.3 |

[1] 250 ppm synthetic hard water (solvent used for chlorine species)
[2] MCU = Monochlorourea (per Example 3)
[3] Bleach = Reagent Grade (13.8%) Sodium Hypochlorite Example 4

The stability of the chlorourea and chlorourea derivatives in the presence of chlorine demand is significantly different than that of bleach or chloroamines. This can be seen in Table 4 below. 20 mL aliquots of a 0.1× nutrient broth were used and the active species added such that the initial concentration of each was equivalent to 5 ppm chlorine as measured by the Hach. To prepare the nutrient broth Difco Nutrient Broth (8 grams) was dissolved in 1 L of deionized water, and subsequently diluted to 0.1× of the initial concentration prior to being autoclaved at 121° C. for 15 minutes. 100 mL solutions of each of the actives were made, and the concentration was measured using standard Hach test procedures on a BetzDearborn DR 2010 Spectrophotometer. At each time point a 1:10 dilution of the solution in DI water was made and placed in the spectrophotometer cell. Hach Permachem DPD Total Chlorine Reagent was added and the cell was placed into the spectrophotometer. The ppm of $Cl_2$ was measured at 0, 1, 3, 6, 24, and 48 hours. A fresh dilution was made at each time point, if necessary, and the bottles of solution were placed in a shaking incubator at 37° C. in between runs. Dimethyl monochlorourea is notated as DMCU. Bis-hydroxymethyl chlorourea is BHMCU.

TABLE 4

Comparison of the stabilities of bleach and monochloramine to chlorourea (MCU) and chlorourea derivatives.

| | 0 hr | 1 hr | 3 hrs | 6 hrs | 24 hrs | 48 hrs | 72 hrs |
|---|---|---|---|---|---|---|---|
| monochloramine | 100% | | 24% | 6% | 2% | 1% | |
| Bleach | 100% | | 22% | 6% | 2% | 1% | |
| DMCU | 100% | | 87% | 87% | 72% | 58% | |
| MCU | 100% | | 81% | 80% | 61% | 46% | |
| BHMCU | 100% | 70% | 49% | 38% | | | 3% |

Example 5

Monochlorourea was synthesized by adding methanol (30 mL) to a 100 mL round bottom flask equipped with a magnetic stir bar, and the whole was cooled in a salt-ice bath to 0° C. Another aliquot of methanol (10 mL) was added to a small vial which was subsequently sealed and cooled to 0° C. Urea (0.76 g, 12.63 mmol) was added to the flask and stirred into solution. T-butyl hypochlorite (0.96 mL, 8.84 mmol) was diluted in the vial with methanol, and this solution was subsequently added slowly to the urea solution, drop wise, over a period of five to ten minutes. The combined solution was stirred for another fifteen minutes, after which, the ice bath was removed and the reaction brought to room temperature for one hour. The solvent was removed in vacuo, resulting in a white solid. The solid was characterized by $^{13}$C NMR which yielded the speciation shown in Table 5. This crude solid can be enriched further by precipitation from methanol into hexanes. The enriched material contains 70% monochlorourea and 30% urea.

TABLE 5

Distribution of chemical species after the slow
addition of t-butyl hypochlorite to a urea solution.

| Species | Mole % | Wt % |
|---|---|---|
| Urea | 42.3 | 36.6 |
| Monochlorourea | 39.5 | 53.8 |
| Methanol | 16.1 | 7.4 |
| t-butanol | 2.1 | 2.2 |

Example 6

The efficacy of monochlorourea as a biocide, as synthesized in Example 1, was tested against the bacterium *Pseudomonas aeruginosa*. The Hach DPD chlorine test (Hach Company, Loveland, Colo.) was used to measure the total available chlorine concentrations of each biocide tested. Concentrations are reported in units of milligrams per liter as $Cl_2$. *P. aeruginosa* was grown overnight in Trypticase Soy Broth at 37° C. The culture was split into aliquots of equal volume, suspended in physiologically buffered saline (PBS). In this example, the cultures were exposed to 1.0 mg/mL, 5.0 mg/L, 10.0 mg/L, and 15.0 mg/L of biocide for 60 minutes. The cultures were then evaluated by measuring viable cell counts after exposure to the biocides. Table 6 shows the results from tests done comparing monochlorourea and sodium hypochlorite.

TABLE 6

A comparison of the reduction in viability of cultures of *P. aeruginosa*
in PBS induced by monochlorourea (MCU) and hypochlorite (NaOCl).
Values represent $\log_{10}$ of viable cfu/mL remaining after
exposure, and represent the average of three determinations.

| | Untreated Control | 5.0 mg/L | 10.0 mg/L | 15.0 mg/L |
|---|---|---|---|---|
| MCU | 9.4 | 4.0 | 2.7 | 2.3 |
| NaOCl | 9.7 | 9.7 | 9.1 | 4.4 |

Example 7

N-chloro-N,N'-dimethylurea was synthesized by adding methanol (60 mL) to a 250 mL round bottom flask equipped with a magnetic stir bar without cooling. Another aliquot of methanol (20 mL) was added to a small vial. N,N'-dimethylurea (2.0 g, 24.37 mmol) was added to the flask and stirred into solution. T-butyl hypochlorite (2.21 mL, 19.50 mmol) was diluted in the vial with methanol, and this solution was subsequently added to the urea solution over a period of less than five minutes. The combined solution was stirred for up to another two hours. The solvent was removed in vacuo, resulting in a colorless and transparent oil. The solid was characterized by $^1$H NMR which indicated it was 70% N-chloro-N,N'dimethylurea. This crude material can be purified by flash chromatography ($R_f$=0.65) on silica with ethyl acetate. The purified material contains >95% of the desired product.

Example 8

The efficacy of dimethyl monochlorourea (DMCU) as a biocide, as synthesized in Example 5, was tested against the bacterium *Pseudomonas aeruginosa*. The Hach DPD chlorine test (Hach Company, Loveland, Colo.) was used to measure the total available chlorine concentrations of each biocide tested. Concentrations are reported in units of milligrams per liter as $Cl_2$. *P. aeruginosa* was grown overnight in Trypticase Soy Broth at 37° C. The culture was split into aliquots of equal volume and suspended in physiologically buffered saline (PBS). In this example, the cultures were exposed to 1.0 mg/mL, 5.0 mg/l, 10.0 mg/l, and 15.0 mg/l of biocide for 60 minutes. The cultures were then evaluated by measuring viable cell counts after exposure to the biocides. Table 7 shows the results from tests done comparing monochlorourea and sodium hypochlorite.

TABLE 7

A comparison of the reduction in viability of cultures of *P. aeruginosa*
in PBS induced by dimethyl monochlorourea (DMCU) and hypochlorite
(NaOCl). Values represent $\log_{10}$ reduction of viable cfu/mL,
and represent the average of three determinations.

| | mg/L | 0.3 | 0.9 | 1.5 |
|---|---|---|---|---|
| DMCU | LR | 0.45 | 1.49 | 3.99 |
| | mg/L | 1 | 3 | 5 |
| NaOCl | LR | 5.3 | 5.4 | 6.7 |

Example 9

N-chloro-N,N'-bishydroxymethylurea can be synthesized in the same manner as N-chloro-N,N'-dimethylurea. The bishydroxyurea (1.0 g, 8.33 mmol) was added to methanol (60 mL) in a 250 mL round bottom flask equipped with a magnetic stir bar without cooling. Another aliquot of methanol (20 mL) was added to a small vial. T-butyl hypochlorite (0.75 mL, 6.66 mmol) was diluted in the vial with methanol, and this solution was subsequently added to the urea solution over a period of less than five minutes. The combined solution was stirred for up to another two hours. The solvent was removed in vacuo, resulting in a colorless and transparent oil that solidified upon prolonged standing. The solid was characterized by $^1$H NMR which indicated it was 20-30% N-chloro-N,N'-bishydroxymethylurea. Table 8 shows the reduction in viability of cultures exposed to bishydroxymethylurea.

TABLE 8

Log reduction in populations of *Pseudomonas aeruginosa*
and *Staphylococcus warneri* exposed to 0.3 ppm
(*P. aeruginosda*) or 1.5 ppm (*S. warneri*) bishydroxymethylurea
after a 1 or 2 hour exposure. Values are the average
of two determinations.

| | Log Reduction | |
|---|---|---|
| Microbe | 1 hr | 2 hr |
| P. aeruginosa | 3.63 | 6.98 |
| S. warneri | 6.37 | 6.52 |

Example 10

This example demonstrates the efficacy of monochlorourea in paper mill process water. Paper mill process water samples were collected from a paper mill producing super calendered paper Samples were inoculated with *P. aeruginosa*, and then dosed with monochlorourea and sodium hypochlorite and plated after 60 minutes. The results are shown in Table 9.

TABLE 9

A comparison of the reduction in viability of cultures of *P. aeruginosa* in papermill process water induced by monochlorourea (MCU) and hypochlorite (NaOCl). Number represent $\log_{10}$ of viable cfu/mL, and represent the average of three values.

|  | Untreated Control | 1.0 mg/l | 3.0 mg/l | 5.0 mg/l | 10.0 mg/l |
|---|---|---|---|---|---|
| MCU | 9.9 | 9.9 | 4.3 | 3.2 | 3.1 |
| NaOCl | 9.9 | 9.9 | 9.8 | 8.7 | 4.5 |

Example 11

The effect of pH on the stability of monochlorourea was significant. Carbon 13 labeled urea was used to examine the stability of the products overnight in $D_2O$. Under basic conditions the chlorourea exhibited limited stability, and in 12 hours no peak in the $^{13}C$ NMR from chlorourea could be detected. However, completely acidifying all the solutions to a pH of 2.5 did have a significant effect on both the yield and the stability of the product. The monochlorourea generated and stored under acidic conditions gave no indication by $^{13}C$ NMR of any decomposition overnight.

Example 12

The stability of dimethylchlorourea was also examined under a variety of different conditions including pH and temperature. As can be seen in Table 10 the material is stable under both acidic and basic conditions at room temperature, with half lives between 2 and 100 days. In the following table the initial concentration $C_0$, the final concentration $C_f$, the final time $t_f$ and the half life $t\frac{1}{2}$, are given.

TABLE 10

Stability of dimethylchlorourea aqueous solutions at different pH and temperature ranges as measured by UV-Vis Spectroscopy.

| Temp ° C. | pH | $C_0$ ppm | $C_f$ ppm | $t_f$ | $t\frac{1}{2}$ |
|---|---|---|---|---|---|
| RT | 2 | 393 | 220 | 34 | 41 Days |
| RT | 3 | 577 | 402 | 28 | 54 Days |
| RT | 5 | 603 | 456 | 34 | 84 Days |
| RT | 7 | 590 | 474 | 33 | 104 Days |
| RT | 9 | 589 | 475 | 33 | 106 Days |
| RT | 12 | 423 | 280 | 1 | 2 Days |
| 50 | 3 | 575 | 491 | 1 | 4 Days |
| 50 | 5 | 576 | 561 | 3 | 82 Days |
| 50 | 12 | 478 | 315 | 6 | 10 Hours |
| 75 | 3 | 576 | 231 | 24 | 18 Hours |
| 75 | 7 | 590 | 562 | 1 | 14 Days |
| 75 | 12 | 423 | 4 | 24 | 4 Hours |

RT means room temperature

What is claimed is:

1. A process comprising the step of adding an aqueous solution of monochlorourea or modified monochforourea to an industrial water system to control the growth of microorganisms wherein the solution of monochlorourea or modified monochlorourea is characterized such that greater than 20% of solids on a molar basis are monochlorourea or modified monochlorourea.

2. The process of claim 1 wherein the modified monochlorourea comprises N-chloro-N,N'-dimethylurea.

3. The process of claim 1 wherein the modified monochforourea comprises N-chloro-N,N'-bishydroxymethylurea.

4. The process of claim 1 wherein the modified monochlorourea comprises N-chloro-N-methylurea.

5. The process of claim 1 wherein the modified monochlorourea comprises N-chloro-N',N'-dimethylurea.

6. The process of claim 1 wherein the concentration of monochlorourea or modified monochlorourea in the industrial water, as measured by the amount of available chlorine, ranges from 0.1 mg/l to 20.0 mg/l.

7. The process of claim 1 wherein the pH of the aqueous solution of monochlorourea or modified monochlorourea ranges from 2 to 8.

8. The process of claim 1 where in the monochlorourea or modified monochlorourea has the formula of:

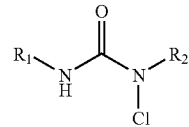

where $R_1$ and $R_2$, independently are H, alkyl, aryl or functionalized alkyl chains having between 1 and 10 carbon atoms, and wherein the alkyl or aryl group is linear or branched.

9. The process of claim 8 wherein the functional groups are selected from the groups consisting of $CH_3$, $NO_2$, COOH, $NH_2$, Cl, Br, $SO_3H$ and OH.

10. The process of claim 8 wherein where $R_1$ and $R_2$, independently are H, methyl or functional methyl.

11. The process of claim 1 wherein the concentration of monochlorourea or modified monochlorourea in the industrial water, as measured by the amount of available chlorine, ranges from 0.5 mg/l to 200.0 mg/l.

12. The process of claim 1 wherein the concentration of monochlorourea or modified monochlorourea in the industrial water, as measured by the amount of available chlorine, ranges from 0.1 mg/l to 100.0 mg/l.

13. The process of claim 1 wherein the concentration of monochlorourea or modified monochlorourea in the industrial water, as measured by the amount of available chlorine, ranges from 0.1 mg/l to 10.0 mg/l.

14. The process of claim 1 wherein the pH of the aqueous solution of monochlorourea or modified monochlorourea ranges from 2 to 5.

15. The process of claim 1 wherein the active solids on a dry basis of the aqueous solution of monochlorourea or modified monochlorourea is at least 30%.

16. A process comprising the step of adding an aqueous solution of N-chloro-N,N'-dimethylurea to an industrial water system to control the growth of microorganisms wherein the aqueous solution has greater than 20% solids on a molar basis, wherein the concentration of N-chloro-N,N'-dimethylurea in the industrial water, as measured by the amount of available chlorine, ranges from 0.1 mg/l to 100.0 mg/l.

* * * * *